(12) United States Patent
Wang et al.

(10) Patent No.: US 8,040,756 B2
(45) Date of Patent: Oct. 18, 2011

(54) RESONANCE ULTRASONIC TRANSDUCER (75) Inventors: Hua Wang, Chongqing (CN); Feng Wu, Chongqing (CN); Hai Wang, Chongqing (CN); Siyuan Yan, Chongqing (CN)

(73) Assignee: Chongqing Ronghai Medical Ultrasound Industry Ltd., Chongqing (CN)

( * ) Notice: Subject to any disclaimer, the term of this patent is extended or adjusted under 35 U.S.C. 154(b) by 325 days.

(21) Appl. No.: 12/439,590

(22) PCT Filed: Feb. 13, 2007

(86) PCT No.: PCT/CN2007/000513
§ 371 (c)(1),
(2), (4) Date: Mar. 2, 2009

(87) PCT Pub. No.: WO2008/028373
PCT Pub. Date: Mar. 13, 2008

(65) Prior Publication Data
US 2009/0259129 A1 Oct. 15, 2009

(30) Foreign Application Priority Data

Sep. 4, 2006 (CN) .......................... 2006 1 0128644

(51) Int. Cl.
*A61B 8/14* (2006.01)
*A61N 7/00* (2006.01)
*G01N 29/00* (2006.01)
(52) U.S. Cl. ....................................... 367/140

(58) Field of Classification Search .................. 367/151, 367/140; 600/459
See application file for complete search history.

(56) References Cited

U.S. PATENT DOCUMENTS

| 3,948,350 | A | * | 4/1976 | Erickson | 367/151 |
| 4,795,935 | A | | 1/1989 | Fujii et al. | |
| 2006/0241524 | A1 | * | 10/2006 | Lee et al. | 601/2 |
| 2009/0259129 | A1 | * | 10/2009 | Wang et al. | 600/459 |

FOREIGN PATENT DOCUMENTS

| DE | 3131796 A1 | | 2/1983 |
| EP | 2064994 A1 | * | 6/2009 |
| JP | 6102260 A | | 4/1994 |

* cited by examiner

*Primary Examiner* — Daniel Pihulic
(74) *Attorney, Agent, or Firm* — The Webb Law Firm (57) ABSTRACT

The present invention provides a resonance ultrasonic transducer. The resonance ultrasonic transducer comprises an ultrasound source for transmitting ultrasound, and a reflecting unit disposed opposite to the ultrasound source. The ultrasound source and the reflecting unit constitute a resonance cavity. The reflecting unit can also act as an ultrasound source. A specific distribution of the acoustic field may be formed in the resonance cavity by matching the transmitting acoustic field of one ultrasonic transducer with the reflecting acoustic field of the other ultrasonic transducer. This resonance ultrasonic transducer can be widely used in ultrasonic diagnosis device, ultrasonic therapy device and ultrasonic detection device, and carries out effective focusing and controlling of an ultrasonic field.

19 Claims, 5 Drawing Sheets

RESONANCE ULTRASONIC TRANSDUCER

FIELD OF THE INVENTION

The present invention relates to an ultrasonic transducer and, particularly, to a resonance ultrasonic transducer with a resonance cavity ultrasonic distribution mode.

BACKGROUND OF THE INVENTION

The ultrasonic emission efficiency of ultrasonic transducer can be improved by superposition of the ultrasonic waves emitted from an ultrasonic transducer and the reflected ultrasonic waves. In its designs of reflecting ultrasonic confocal microscope, Japanese patent No. JP6102260 adopts this method to increase acoustic fields at the sample to be observed so as to improve the imaging quality of ultrasonic microscope.

German patent No.: DE3131796 (Title of the invention: Scanning ultrasonic microscope) adopts two confocal spherical shell ultrasonic transducers, which have a common focal point. One transducer acts as ultrasound source for transmitting ultrasonic waves and the other acts as a receiver for receiving ultrasonic waves which obtains the image of the substance from the received signals.

However, the two patents as mentioned above only disclosed that using two ultrasonic transducers or one of them replaced by a reflector so as to increase the acoustic field at the focal point of microscope, but the ultrasonic emission efficiency of ultrasonic transducer hasn't been improved in a vast scale.

SUMMARY OF THE INVENTION

Aiming at the disadvantages of the prior art as mentioned above, the present invention provides a resonance ultrasonic transducer, which can form a specific distribution of acoustic field. By forming an ultrasonic resonance cavity with special parameters, the transmitting acoustic field of one ultrasonic transducer is matched with the reflecting acoustic field of another ultrasonic transducer and accordingly a specific ultrasonic field, such as high focused ultrasonic focusing field can be formed in a resonance cavity.

The technical solutions for the problems proposed by the present invention is the resonance ultrasonic transducer, which comprises an ultrasound source for transmitting ultrasonic waves and a reflecting unit disposed oppositely to said ultrasound source. Said ultrasound source and reflecting unit constitute a resonance cavity.

After constituting a resonance cavity, the ultrasonic waves transmitted from ultrasound source will be reflected repeatedly between the ultrasound source and the reflecting unit and thus a resonance is formed. Therefore, said ultrasound source in the present invention can also act as a reflecting unit.

Preferably, said reflecting unit can be achieved by an ultrasound source with reflection function.

Such two ultrasound transducers are arranged oppositely and the acoustic field formed in the cavity is not the simple superposition of two acoustic fields of two ultrasound transducers arranged oppositely, but the coherent superposition of the ultrasonic fields formed by repeat reflection of the end faces of two ultrasound transducers arranged oppositely and transmitting of ultrasound source. The distribution of the acoustic field formed by superposition is jointly determined by the distance between the two ultrasound transducers arranged oppositely, the caliber and focal distance of ultrasound transducers, the reflecting capacity of the surfaces of ultrasound transducers and the acoustic parameters of medium between ultrasound transducers. The distribution of acoustic field formed by the superposition can be analyzed by the similar method of optical resonance cavity, that is, a specific distribution of ultrasonic field transmitted from ultrasonic transducer can be formed by means of setting up the parameters for ultrasonic resonance cavity. Because the effective caliber of the focusing acoustic field formed in ultrasonic resonance cavity is bigger than the effective caliber of a single ultrasonic transducer, the acoustic field of transducer, especially the focused ultrasonic transducer, can be more concentrated by means of setting up the parameters of the shape of the resonance ultrasonic transducer and the parameters of the relationship between transducers. This kind of resonance ultrasonic transducer with a high energy utilization rate and the high signal-to-noise ratio can be used for ultrasonic diagnosis, ultrasonic therapy and ultrasonic detection.

The basic principle of the present invention is as follows:

The forming mechanism of resonance ultrasonic transducer in the present invention is similar to the distribution of light waves in the optical resonance cavity. Because in the ultrasound therapy and measurement, the medium contacted with ultrasonic transducer is liquid medium or human body tissue, but the ultrasonic wave, which is a kind of mechanical wave, mainly represent as longitudinal wave in the liquid medium and human body tissue. When the ultrasonic wave is transmitted at the interface of two kinds of substances, reflection and refraction will occur. The rules of reflection and refraction meet Snell Law. The wave equation met in resonance cavity is consistent with scalar wave equation of light wave.

$$c^2 \frac{\partial^2 p}{\partial t^2} = \nabla^2 p \tag{1}$$

Wherein, p is sound pressure; c is sound velocity of the medium in cavity.

Figure 1:
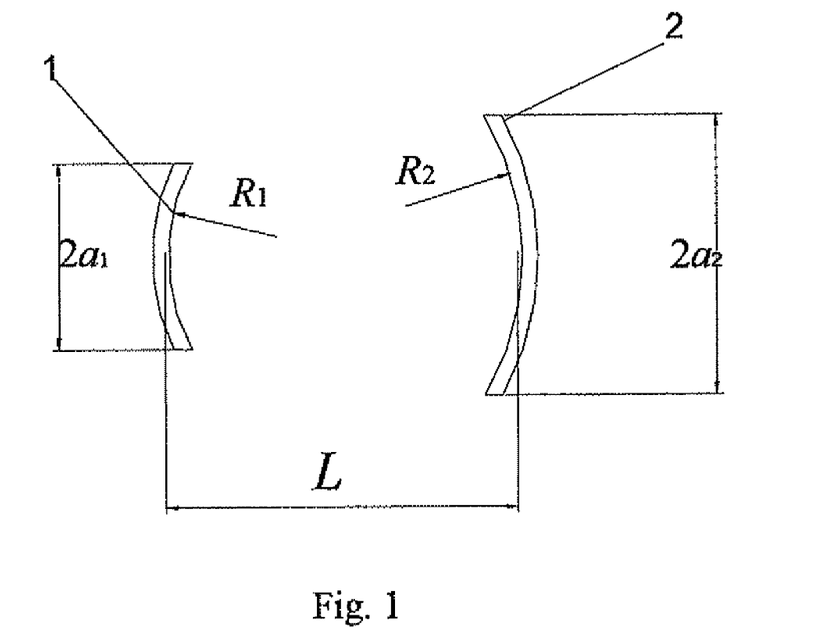
FIG. 1 is a structural diagram of resonance ultrasonic transducer of the embodiment 1 of the present invention.

As shown in FIG. 1, when two ultrasound sources arranged oppositely, that is, the first ultrasound source 1 and the second ultrasound source 2 are placed coaxially (wherein, one of the ultrasound sources may be ultrasonic reflecting unit), the medium, in which the ultrasound can be transmitted, is filled in the space between the two ultrasound sources. Because the ultrasound sources can transmit and reflect ultrasonic wave, two ultrasound sources form an ultrasonic resonance cavity. The distribution of acoustic field in the resonance cavity is the superposition of the direct transmitting acoustic field of the transducer and the reflecting acoustic field of the surface of the transducer.

The working mode of the resonance cavity of the first ultrasound source and the second ultrasound source will influence the distribution of acoustic fields in the resonance cavity greatly. Only an acoustic field with specific distribution can exist steadily in this kind of resonance cavity. Because the time for establishment of a steady acoustic field is short, the acoustic field keeps steady only in the case of an acoustic field with specific distribution existing in resonance cavity. These acoustic fields with specific distribution in resonance cavity are related to the parameters of resonance cavity and they can be described by modes of acoustic fields. Because the distribution of acoustic fields can be divided into spatial distribution and time distribution, the steady acoustic fields existing in resonance cavity can be represented by time mode or spatial mode (respectively corresponding to longitudinal mode and transverse mode of optical resonance cavity). The time mode corresponds to the frequency limit of these acoustic fields. If a steady distribution of acoustic fields is to be formed in the resonance cavity, the working frequency of the first ultrasound source and the second ultrasound source must be specific frequency values. These specific frequency values are related to the length of resonance cavity. The ultrasound frequency steadily existing in resonance cavity is as follows:

$$f = \frac{kc}{2L} \quad (2)$$

$$k = \text{Integer}$$

Wherein, f is the frequency, c is the sound velocity of the medium and L is the distance between two transducers (i.e. the length of resonance cavity).

If a steady distribution of acoustic fields is to be formed in the resonance cavity, apart from the frequency condition of ultrasonic waves, the spatial distribution condition (spatial mode) must be met too, because the steady distribution of ultrasonic waves in the resonance cavity is the result of superposition of the acoustic fields reflected repeatedly by the two reflecting surfaces which constitute the resonance cavity and the transmitting acoustic field of ultrasound source. Therefore, the ultrasonic wave starts from one reflecting surface and transmits to the other reflecting surface and then is reflected and transmits back to the initial reflecting surface. The distribution of ultrasonic fields on the reflecting surface should be the same as it starts. Just as the flowing equation:

$$\gamma_1 p_1(x_1, y_1) = -\frac{i}{\lambda L} \int\int_{s_2} p_2(x_2, y_2) \exp(-ikr) dx_2 dy_2 \quad (3)$$

$$\gamma_2 p_2(x_2, y_2) = -\frac{i}{\lambda L} \int\int_{s_1} p_1(x_1, y_1) \exp(-ikr) dx_1 dy_1$$

$$r \approx \sqrt{L^2 + (x_1 - x_2)^2 + (y_1 - y_2)^2}$$

$$k = \frac{2\pi}{\lambda}$$

Figure 2:
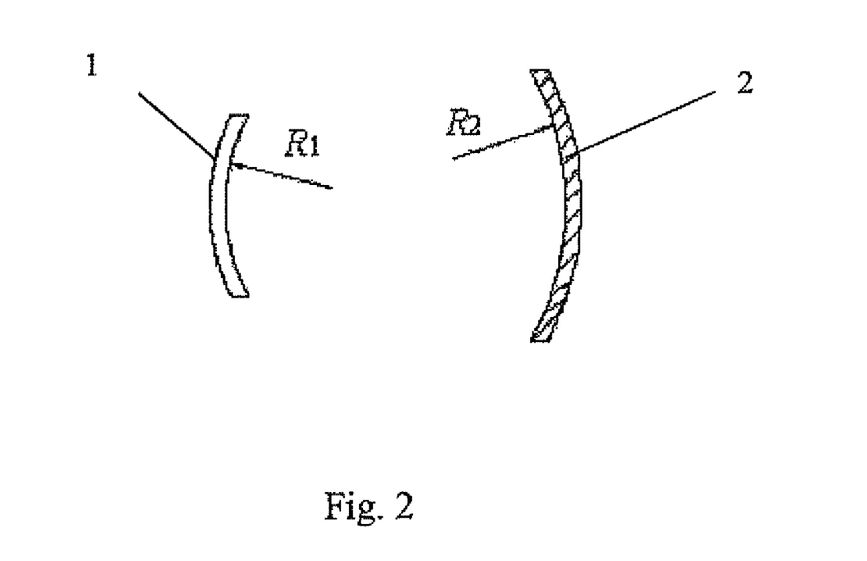
FIG. 2 is a relationship diagram of acoustic fields of resonance cavity surface.

Wherein, $p_1(x_1,y_1)$ is the acoustic pressure distribution of the reflecting surface of the first ultrasound source; $p_2(x_2,y_2)$ is the acoustic pressure distribution of the reflecting surface of the second ultrasound source (as shown in FIG. 2), wherein, $(x_1,y_1)$ and $(x_2,y_2)$ are respectively the coordinates of transducer's cavity surface of the resonance cavity, $\gamma_1$ and $\gamma_2$ are respectively the reflecting coefficient of ultrasonic wave of two cavity surfaces and $\lambda$ is the ultrasonic wavelength in resonance cavity.

Because formula (3) is an integral equation set. This equation set should be solved by numerical method. But under special conditions, this equation set may obtain an analytic solution, for example, when the outer frame of piezoelectric crystal is a rectangle frame and L is long enough for setting the surface of resonance cavity as a flat plane when calculating the distance of "r", then the distribution of acoustic fields on its surface is:

$$P_{1mn} = P_{10} \exp\left(\frac{x_1^2 + y_1^2}{W_1^2}\right) H_m\left(\sqrt{2} \frac{x_1}{W_1}\right) H_n\left(\sqrt{2} \frac{y_1}{W_1}\right) \quad (4)$$

-continued $$P_{2mn} = P_{20} \exp\left(\frac{x_2^2 + y_2^2}{W_2^2}\right) H_m\left(\sqrt{2} \frac{x_2}{W_2}\right) H_n\left(\sqrt{2} \frac{y_2}{W_2}\right)$$

$$W_1^2 = \frac{\lambda L}{\pi} \left[\frac{g_2}{g_1(1 - g_1 g_2)}\right]^{1/2}$$

$$W_2^2 = \frac{\lambda L}{\pi} \left[\frac{g_1}{g_2(1 - g_1 g_2)}\right]^{1/2}$$

$$g_i = 1 - \frac{R_i}{L}$$

$$i = 1.2$$

Wherein, $P_{10}$, $P_{20}$ respectively correspond to the amplitudes of acoustic field of ultrasonic waves in the center of the first ultrasound source 1 and the second ultrasound source 2; $R_1$, $R_2$ respectively correspond to the radiuses of the first ultrasound source 1 and the second ultrasound source 2; $P_{1mn}$, $P_{2mn}$ respectively correspond to the distributions of acoustic fields of the first ultrasound source 1 and the second ultrasound source 2 with a mode symbol of "m" in horizontal direction and a mode symbol of "n" in vertical direction (m, n=0, 1, 2, 3, . . . ).

$H_m$ (.) is m order Hankel function.

In the resonance cavity, the formed steady acoustic field at the resonance cavity surface should meet the formula (3). When the shape of resonance cavity is rectangle and the near axial approximation may be applied, the formed steady acoustic field at the resonance cavity surface should meet the formula (4).

Figure 3:
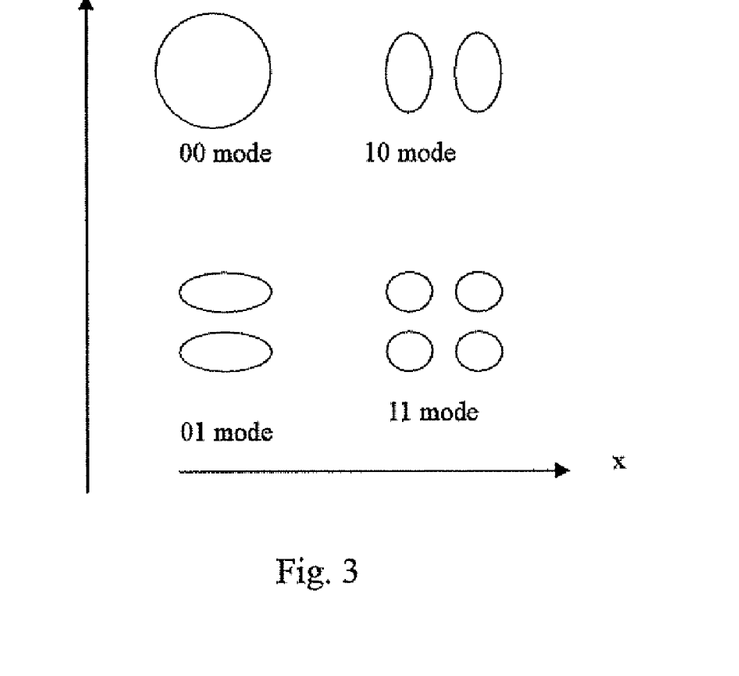
FIG. 3 is a mode diagram of low order steady distribution of sound pressure of square piezoelectric crystal.

FIG. 3 shows the low order steady distribution of sound pressure on the reflector surface when the outer shape of resonance cavity is square piezoelectric crystal (represented by modes), the modes in this figure are orders of Hankel function (i.e. m, n in formula (4)).

When the frame of piezoelectric crystal is round, its distribution on the reflector surface can still be represented by analytic form and the distribution of sound pressure on the surface of ultrasound transducer is;

$$P_{1mn}(r_1, \phi_1) = \exp(-r_1^2/W_1^2) \left[\frac{\sqrt{2} r_1}{W_1}\right]^n L_m^{(n)}(-2r_1^2/W_1^2) \begin{cases} \cos n\phi_1 \\ \sin n\phi_1 \end{cases} \quad (5)$$

$$P_{2mn}(r_2, \phi_2) = \exp(-r_2^2/W_2^2) \left[\frac{\sqrt{2} r_2}{W_2}\right]^n L_m^{(n)}(-2r_2^2/W_2^2) \begin{cases} \cos n\phi_2 \\ \sin n\phi_2 \end{cases}$$

Figure 4:
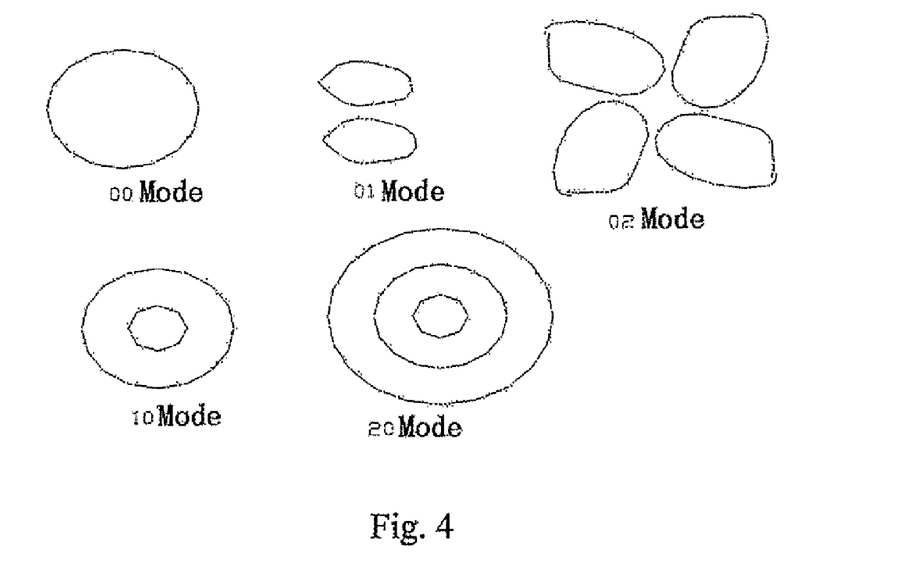
FIG. 4 is a mode diagram of low order steady distribution of sound pressure of round piezoelectric crystal.

Wherein, $L_m^{(n)}$ is Laguerre polynomial; $r_1$, $r_2$, $\Phi_1$, $\Phi_2$ respectively represent the polar coordinates of the ultrasound transducer surfaces $S_1$ and $S_2$. The steady distribution of acoustic field must meet the formula (5). FIG. 4 shows the steady distribution modes of sound pressure on the reflector surface (low order) when the shape is round piezoelectric crystal, the mode figures in this figure are m and n in formula (5).

Figure 5:
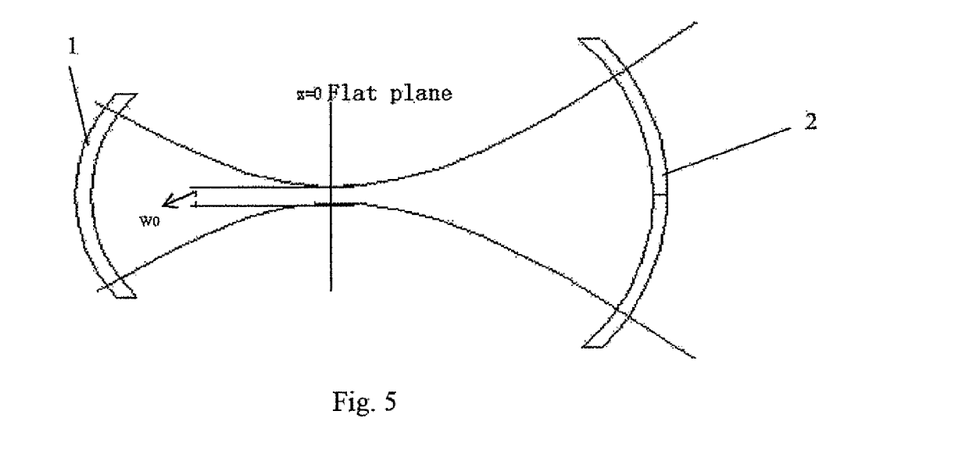
FIG. 5 is a mode diagram of distribution of steady acoustic field having a Gauss distribution in resonance cavity.

The determined distribution on cavity surface corresponds to a steady distribution in cavity. According to wave equation, the distribution of ultrasonic waves in resonance cavity has a Gauss distribution as shown in FIG. 5. Because the lowest order mode has good directivity, concentrated energy and less acoustic loss, the low order mode, that is, fundamental mode is always used in the ultrasound therapy and detection. $W_0$ is the radius of spot of acoustic beams in resonance cavity, under the condition of fundamental mode, the distribution of acoustic field in resonance cavity is:

$$P(z, r) = \frac{P_0}{1 - iz/z_0} \exp\left(-\frac{r^2/W_0^2}{1 - iz/z_0}\right) \quad (6)$$

Wherein, $z_0$ is a constant and $z_0 = W_0^2 \pi / \lambda_0$.

In the ultrasonic therapy, because the maximum gain is required at the focal point (position of spot size) of ultrasonic waves, the minimum radius of spot is required. Therefore, the relationship between the radius of spot and the parameters of resonance cavity should be known. When the reflecting surfaces of piezoelectric crystal constitute different types of resonance cavities, the relationships between the radius of spot and the parameters of resonance cavity are different. This relationship between them may be shown as follows:

$$w_0 \sqrt{\frac{\lambda}{\pi}} \frac{[L(R_1 - L)(R_2 - L)(R_1 + R_2 - L)]^{1/4}}{(R_1 + R_2 - 2L)^{1/2}} \quad (7)$$

The distance from the spot to the surface of ultrasound transducer is:

$$l_1 = \frac{L(R_2 - L)}{R_1 + R_2 - 2L} \quad (8)$$

$$l_2 = \frac{L(R_2 - L)}{R_1 + R_2 - 2L}$$

Wherein, $l_1$ and $l_2$ respectively represent the distances from the spot to the surface of the first ultrasound source (piezoelectric crystal) 1 and the surface of the second ultrasound source (piezoelectric crystal) 2, that is, the distances from the focal point to the surfaces of two piezoelectric crystals. According to the cavity surface radiuses of ultrasound transducers and the distance between two transducers (length of cavity), the resonance transducer can be divided into a symmetrical one, a confocal one, a concentric one, and a concentric and symmetrical one, etc. The relationship between the radius of these resonance cavities and the length of cavity is as follows:

Symmetrical: $R_1 = R_2$
Confocal: $L = (R_1 + R_2)/2$
Concentric: $L = (R_1 + R_2)$
Concentric and symmetrical: $L = (R_1 + R_2)$, $R_1 = R_2$ The feature of a symmetrical resonance cavity is that the acoustic field is symmetrical along axial direction of resonance cavity, with vertical cavity axis and through the central point of resonance cavity.

The confocal resonance cavity has a short length of cavity and the superposing position of the reflecting acoustic field is at the focal point of the reflecting acoustic field. This kind of resonance cavities can be easily adjusted.

The feature of a concentric resonance cavity is that, theoretically, the superposing centers of all reflections of reflected acoustic waves are the same, but it is hard to adjust them.

The feature of a concentric and symmetrical resonance cavity is that besides the same superposing center, the superposing center is at the center of the sphere, and in principle, the focal point of the focused ultrasound is very small.

According to formula (7), it can be seen that to get the minimum size of the focal point (spot size) is to form a concentric resonance cavity, that is, $(R_1 + R_2 - L) = 0$. The resonance cavity formed by the reflecting surfaces of ochre piezoelectric crystals may have a focal point with a minimum size.

However, in practical use, because the adjustment and assembly of the concentric resonance cavity are difficult, the non-concentric resonance cavity (for example, a confocal resonance cavity) may be applied, but the spot is a little bigger.

However, the ultrasonic resonance cavity constituted by ultrasound sources is different from the common laser resonance cavity. The optical energy in the laser resonance cavity is excited by other different energies and the coherent optical field in the laser resonance cavity is only the laser field. But the acoustic field in ultrasonic resonance cavity is inputted by ultrasonic transducers and the ultrasonic wave of the ultrasound source is fully coherent with the oscillated ultrasonic wave in resonance cavity. The total acoustic field in resonance cavity is equal to the sum of the acoustic field of the ultrasound source and the oscillated acoustic field in resonance cavity. In order to have a single mode in resonance cavity as best as possible, the acoustic field on the output surface of the ultrasound source should be similar to the distribution of acoustic field on the output surface of the ultrasound source of the selected mode in resonance cavity. So, when the fundamental mode is required in resonance cavity, the input acoustic field on the output surface of the ultrasound source should be similar to the distribution of fundamental mode of that surface. When a high order mode is needed, it should be similar to the high order mode distribution.

Acoustic units may be applied in said resonance cavity, for example, the acoustic focusing unit can be used to focus the ultrasonic waves.

Any one of said ultrasound sources has an output window, through which the ultrasonic waves in resonance cavity can be transmitted from the end face of that ultrasonic transducer and thus, the ultrasonic waves in resonance cavity can be applied to the desired place.

Wherein, R and L can be applied with appropriate corresponding values according to the needs of use as long as the corresponding relationship between two parties is met.

The resonance ultrasonic transducer of the present invention can be widely used in devices of ultrasonic diagnosis, ultrasonic therapy, and ultrasonic detection and accomplish effective focusing and controlling of an ultrasonic field.

Said ultrasound sources can adopt focused ultrasound sources or non-focused ultrasound sources according to the needs. For example, in surgery, the focused ultrasound sources can be used to treat liver cancer and etc. For treatment of knee joint pain or other diseases, the non-focused ultrasound sources can be used and mostly, good therapeutic effects can be achieved.

An ultrasonic diagnosis device comprises ultrasonic transducer. Said ultrasonic transducer is the resonance ultrasonic transducer as mentioned above.

An ultrasonic therapy device comprises ultrasonic transducer. Said ultrasonic transducer is the resonance ultrasonic transducer as mentioned above.

An ultrasonic detection device comprises ultrasonic transducer. Said ultrasonic transducer is the resonance ultrasonic transducer as mentioned above.

Wherein: 1-First ultrasound source 2-Second ultrasound source 3-Output window 4-Acoustic unit

DETAILED DESCRIPTION OF PREFERRED EMBODIMENTS

The present invention will be further explained below in detail with reference to the preferred embodiments and accompanying drawings.

The resonance ultrasonic transducer of the present invention comprises an ultrasound source, and a reflecting unit disposed opposite to the ultrasound source. The ultrasound source and the reflecting unit constitute a resonance cavity. Said ultrasound source may also act as a reflecting unit.

The following embodiments are the non-restrictive embodiments of the present invention.

Embodiment 1

This embodiment shows a coaxial working mode of two ultrasonic transducers.

As shown in FIG. 1, in this embodiment, both the ultrasound sources and the reflecting units adopt spherical shell ultrasonic transducers, that is, the first ultrasound source 1 and the second ultrasound source 2. Two spherical shell ultrasonic transducers are placed coaxially and their radiuses are respectively $R_1$ and $R_2$. Setting the length of resonance cavity as L, in order to reduce geometric attenuation and diffraction loss, it is required that $L<R_1+R_2$. $2_{a1}$ and $2_{a2}$ in FIG. 1 respectively stand for the calibers of two ultrasonic transducers.

Two spherical shell ultrasonic transducers can work together or individually. When any one of the transducers works, the other one can only act as a reflector. Or two transducers work alternately.

When these resonance ultrasonic transducers are used for resection treatment and when the target of disease of patient is placed between two transducers, the ultrasound waves are highly concentrated at the spot in resonance cavity due to the reflection of transducer surface. When the target of disease of patient overlaps the spot, the temperature of the target of disease increases to above 60 centigrade and the coagulation necrosis of tissue will occur and accordingly the treatment can be achieved. If the cancer of legs is to be treated, $R_1$ may be 120 mm; $R_2$ may be 110 mm and L may be 200 mm.

Embodiment 2

This embodiment shows a symmetrical working mode of ultrasonic transducers.

Figure 6:
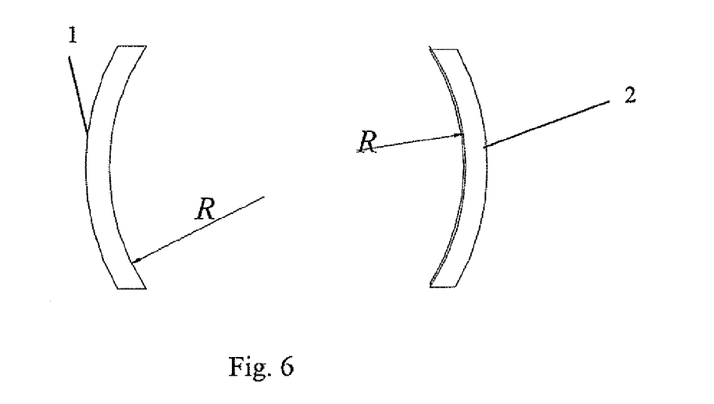
FIG. 6 is a structural diagram of the embodiment 2 of the present invention.

As shown in FIG. 6, in this embodiment, both the ultrasound sources and the reflecting units adopt spherical shell ultrasonic transducers. Two spherical shell ultrasonic transducers are placed coaxially and symmetrically and their radiuses are both R. Setting the length of said resonance cavity as L, in order to reduce geometric attenuation and diffraction loss, it is required that L<2R.

In this embodiment, the spot of the resonance cavity is located right at the center of two ultrasonic transducers. One way to use this embodiment is the same as that in embodiment 1. If the cancer of legs is to be treated, R may be 120 mm and L may be 200 mm.

Embodiment 3

This embodiment shows a concentric working mode of ultrasonic transducers.

Figure 7:
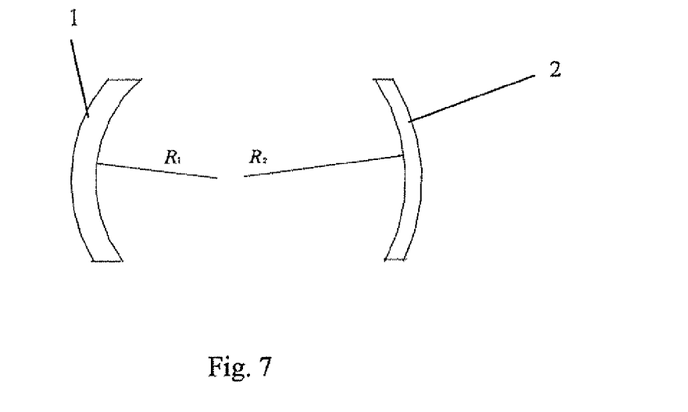
FIG. 7 is a structural diagram of the embodiment 3 of the present invention.

As shown in FIG. 7, in this embodiment, both the ultrasound sources and the reflecting units adopt spherical shell ultrasonic transducers. Two spherical shell ultrasonic transducers are placed coaxially and concentrically. Their radiuses are respectively $R_1$ and $R_2$. Setting the length of resonance cavity as L, it is required that $L=R_1+R_2$. The feature of this kind of device is that the spot size is small. One way to use this embodiment is the same as that in embodiment 1. If the cancer of legs is to be treated, $R_1$ may be 120 mm; $R_2$ may be 110 mm and L may be 230 mm.

Embodiment 4

This embodiment shows a concentric and symmetrical working mode of ultrasonic transducers.

Figure 8:
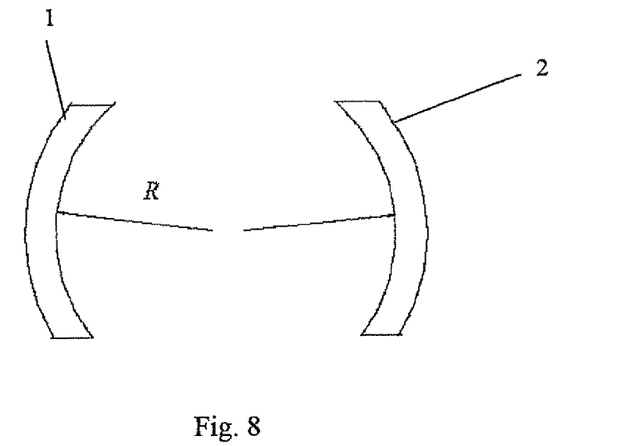
FIG. 8 is a structural diagram of the embodiment 4 of the present invention.

As shown in FIG. 8, in this embodiment, both the ultrasound sources and the reflecting units adopt spherical shell ultrasonic transducers. Two spherical shell ultrasonic transducers are placed coaxially and concentrically and their radiuses are both R. Setting the length of said resonance cavity as L, it is required that L=2R. The feature of this kind of device is that the spot size is small and the spot of the resonance cavity is located right at the center of two ultrasonic transducers. One way to use this embodiment is the same as that in embodiment 1. If the cancer of legs is to be treated, the radius of two transducers "R" is 120 mm and L is 240 mm.

Embodiment 5

This embodiment shows a confocal working mode of ultrasonic transducers.

Figure 9:
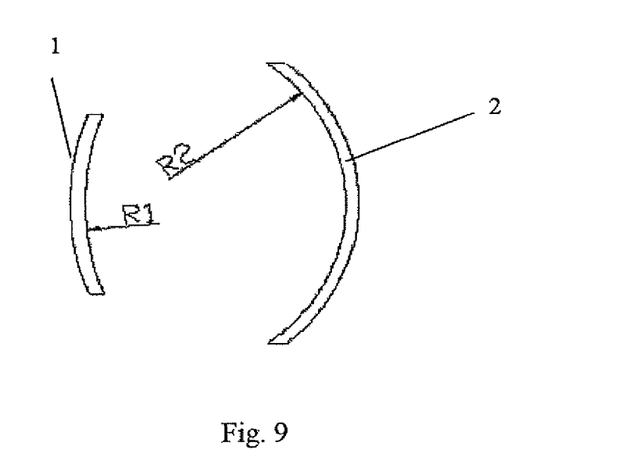
FIG. 9 is a structural diagram of the embodiment 5 of the present invention.

As shown in FIG. 9, said ultrasound source and said reflecting unit are placed confocally. Their radiuses are respectively $R_1$ and $R_2$. Setting the length of resonance cavity as L, at this time, the parameters of resonance cavity have the following relationship: $2L=R_1+R_2$. The spot radius of this resonance cavity is:

$$w_0 = \frac{\lambda L}{2\pi}$$

The resonance ultrasonic transducers constituted by this mode have advantages of small diffraction loss and easy adjustment. One way to use this embodiment is the same as that in embodiment 1. If the cancer of legs is to be treated, $R_1$ may be 120 mm; $R_2$ may be 110 mm and L may be 115 mm.

Embodiment 6

Figure 10:
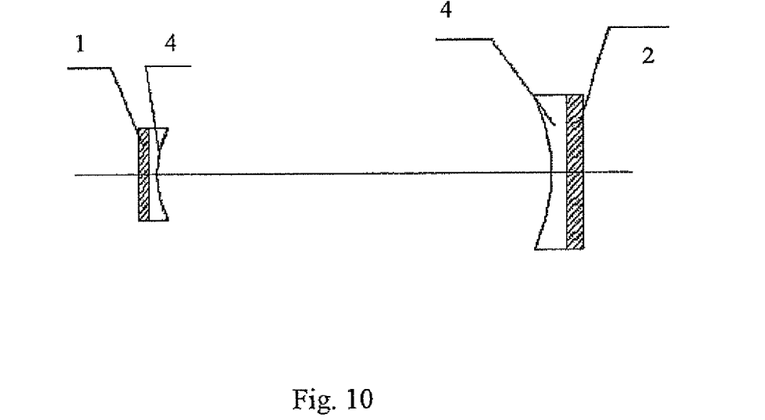
FIG. 10 is a structural diagram of the embodiment 6 of the present invention.

In this embodiment, as shown in FIG. 10, two ultrasonic transducers constitute a resonance cavity. Wherein, two ultrasonic transducers, that is, the first ultrasound source 1 and the second ultrasound source 2 adopt flat piezoelectric transducers. There are acoustic units 4 in resonance cavity and the acoustic units 4 adopt ultrasonic lens. The ultrasonic lenses are arranged in resonance cavity and they contact tightly and respectively with the first ultrasound source 1 and the second ultrasound source 2.

The resonance ultrasonic transducers of this embodiment have a tiny focal point and also have advantages of small diffraction loss and easy adjustment. For this kind of ultrasonic transducer, the designs of ultrasonic lens shall be optimized so that the focusing performance and low reflecting rate can be ensured. One way of use of this embodiment is the same as that in embodiment 1. If the cancer of legs is to be treated and the material for ultrasonic lens is hard aluminum, the radius of lens "$R_1$" may be 120 mm, the radius of lens of reflecting transducer "$R_2$" may be 110 mm and L may be 205 mm (L may vary according to different aluminum alloy materials adopted by ultrasonic lens).

Embodiment 7

Figure 11:
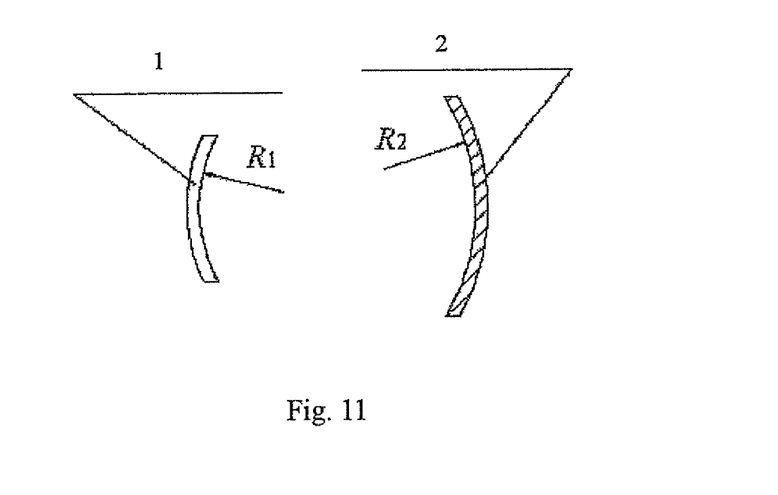
FIG. 11 is a structural diagram of the embodiment 7 of the present invention.

As shown in FIG. 11, in this embodiment the working mode of ultrasound source and reflecting unit can adopt any one of the modes in the embodiments 1 to 6 as mentioned above, but the reflecting unit uses a spherical reflector instead of ultrasonic transducer. One way of use of this embodiment is the same as that in embodiments from 1 to 6.

Embodiment 8

Figure 12:
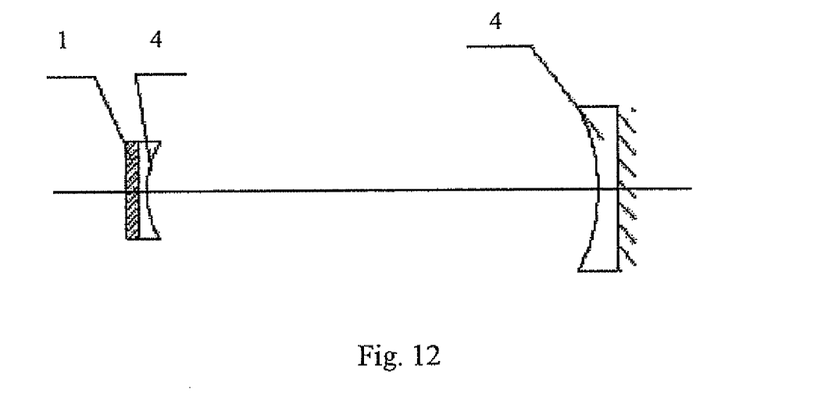
FIG. 12 is a structural diagram of the embodiment 8 of the present invention.

As shown in FIG. 12, in this embodiment, the reflecting unit adopts ultrasonic lens with reflection on rear end face. Other structures are the same as those in embodiment 6. One way to use this embodiment is the same as that in embodiment 6.

Embodiment 9

Figure 13:
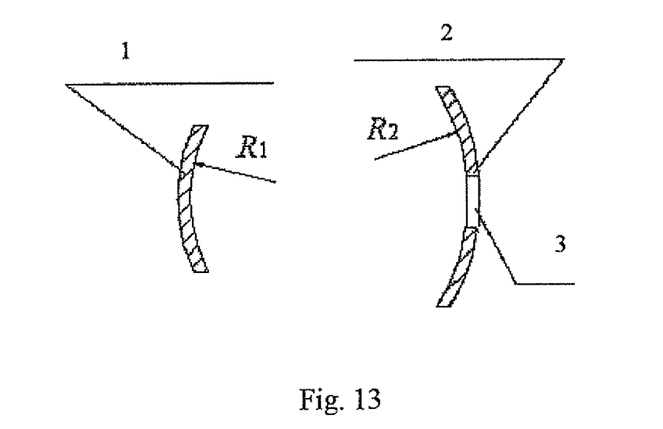
FIG. 13 is a structural diagram of the embodiment 9 of the present invention.

As shown in FIG. 13, the ultrasound sources adopt two ultrasonic transducers. Wherein, an output window 3 is opened on one of the ultrasonic transducers. The output window 3 is made of material with low acoustic impedance (for example, thin plastic membrane). The ultrasonic waves generated by this resonance ultrasonic transducer can be transmitted from the output window 3. This kind of ultrasonic transducer may be applied to ultrasonic wave-guide coupling in bridge detection.

The invention claimed is:

1. A resonance ultrasonic transducer comprising an ultrasound source for transmitting ultrasound, and a reflecting unit disposed oppositely to the ultrasound source; wherein the ultrasound source and the reflecting unit constitute a resonance cavity, and wherein the reflecting unit is the ultrasound source with a function of reflection.

2. The resonance ultrasonic transducer according to claim 1, wherein the ultrasound source and the reflecting unit are placed coaxially and their radiuses are respectively $R_1$ and $R_2$; setting the length of resonance cavity as L, $L<R_1+R_2$.

3. The resonance ultrasonic transducer according to claim 1, wherein the ultrasound source and the reflecting unit are placed coaxially and symmetrically, and their radiuses are both R; setting the length of resonance cavity as L, $L<2R$.

4. The resonance ultrasonic transducer according to claim 1, wherein the ultrasound source and the reflecting unit are placed coaxially and concentrically, and their radiuses are respectively $R_1$ and $R_2$; setting the length of resonance cavity as L, $L=R_1+R_2$.

5. The resonance ultrasonic transducer according to claim 1, wherein the ultrasound source and the reflecting unit are placed coaxially and concentrically, and their radiuses are both R; setting the length of resonance cavity as L, $L=2R$.

6. The resonance ultrasonic transducer according to claim 1, wherein the ultrasound source and the reflecting unit are placed confocally, and their radiuses are respectively $R_1$ and $R_2$; setting the length of resonance cavity as L, $2L=R_1+R_2$.

7. The resonance ultrasonic transducer according to claim 1, wherein the ultrasound source includes a spherical shell ultrasonic transducer and the reflecting unit includes a spherical reflector.

8. The resonance ultrasonic transducer according to claim 1, wherein both the ultrasound source and the reflecting unit include spherical shell transducers.

9. The resonance ultrasonic transducer according to claim 1, wherein acoustic units are included in said resonance cavity.

10. The resonance ultrasonic transducer according to claim 9, wherein the ultrasound sources both include flat piezoelectric transducers; the acoustic units include ultrasonic lens; and the ultrasonic lens are arranged in the resonance cavity and contact tightly with the ultrasound sources.

11. The resonances ultrasonic transducer according to claim 1, wherein at least one of the ultrasound sources has an output window.

12. The resonance ultrasonic transducer as claimed in claim 1, wherein acoustic units are included in the resonance cavity.

13. The resonance ultrasonic transducer according to claim 12, wherein the ultrasound source includes flat piezoelectric transducers; the acoustic units include ultrasonic lenses which are arranged in the resonance cavity and contact tightly with the ultrasound sources.

14. The resonance ultrasonic transducer according to claim 1, wherein the ultrasound source is a focused ultrasound source or a non-focused ultrasound source.

15. An ultrasonic diagnosis device comprising an ultrasonic transducer, wherein the ultrasonic transducer is the resonance ultrasonic transducer as claimed in claim 1.

16. An ultrasonic therapy device comprising an ultrasonic transducer, wherein the ultrasonic transducer is the resonance ultrasonic transducer as claimed in claim 1.

17. An ultrasonic detection device comprising an ultrasonic transducer, wherein the ultrasonic transducer is the resonance ultrasonic transducer as claimed in claim 1.

18. A resonance ultrasonic transducer comprising an ultrasound source for transmitting ultrasound, and a reflecting unit disposed oppositely to the ultrasound source; wherein the ultrasound source and the reflecting unit constitute a resonance cavity, and wherein acoustic units are included in the resonance cavity.

19. The resonance ultrasonic transducer according to claim 18, wherein the ultrasound source includes flat piezoelectric transducers; the acoustic units include ultrasonic lenses which are arranged in the resonance cavity and contact tightly with the ultrasound sources.

* * * * *